(12) United States Patent
Kanbara

(10) Patent No.: US 6,773,420 B2
(45) Date of Patent: Aug. 10, 2004

(54) DEODORIZING FILTER AND COLLECTOR PROVIDED WITH THE DEODORIZING FILTER

(75) Inventor: Noriyuki Kanbara, Soka (JP)

(73) Assignee: Alcare Co., Ltd., Tokyo (JP)

( * ) Notice: Subject to any disclaimer, the term of this patent is extended or adjusted under 35 U.S.C. 154(b) by 108 days.

(21) Appl. No.: 10/185,563

(22) Filed: Jun. 27, 2002

(65) Prior Publication Data

US 2003/0004476 A1 Jan. 2, 2003

(30) Foreign Application Priority Data

Jun. 29, 2001 (JP) .......................................... 2001-198759

(51) Int. Cl.[7] .............................................. A61M 1/00
(52) U.S. Cl. ...................................................... 604/333
(58) Field of Search ................................ 604/332–344

(56) References Cited

U.S. PATENT DOCUMENTS

| | | | | |
|---|---|---|---|---|
| 5,250,042 A | * | 10/1993 | Torgalkar et al. | 604/333 |
| 5,401,264 A | * | 3/1995 | Leise, Jr. | 604/333 |
| 6,328,719 B1 | | 12/2001 | Holtermann et al. | 604/332 |
| 6,506,184 B1 | * | 1/2003 | Villefrance | 604/333 |
| 6,659,988 B1 | * | 12/2003 | Steer et al. | 604/333 |
| 6,709,421 B1 | * | 3/2004 | Falconer | 604/335 |
| 2003/0014023 A1 | * | 1/2003 | Kanbara | 604/333 |

FOREIGN PATENT DOCUMENTS

| | | |
|---|---|---|
| JP | 8103459 | 4/1996 |
| JP | 8150165 | 6/1996 |
| JP | 9253114 | 9/1997 |

\* cited by examiner

*Primary Examiner*—John J. Calvert
*Assistant Examiner*—Michael G. Bogart
(74) *Attorney, Agent, or Firm*—Haverstock, Garrett & Roberts; Veo Peoples, Jr.

(57) ABSTRACT

The present invention provides a deodorizing filter constituted such that the gas permeability thereof is high, the gases generated in an ostomy bag including the gases to be deodorized can be easily discharged, and the sufficient deodorizing ability thereof is sufficiently high. The deodorizing filter is formed so as to incorporate a deodorizing element in a housing and have a gas inlet at one side of the deodorizing element, an outlet at the other side of the deodorizing element, and a space existing at that side of the deodorizing element which faces the ostomy bag.

7 Claims, 3 Drawing Sheets

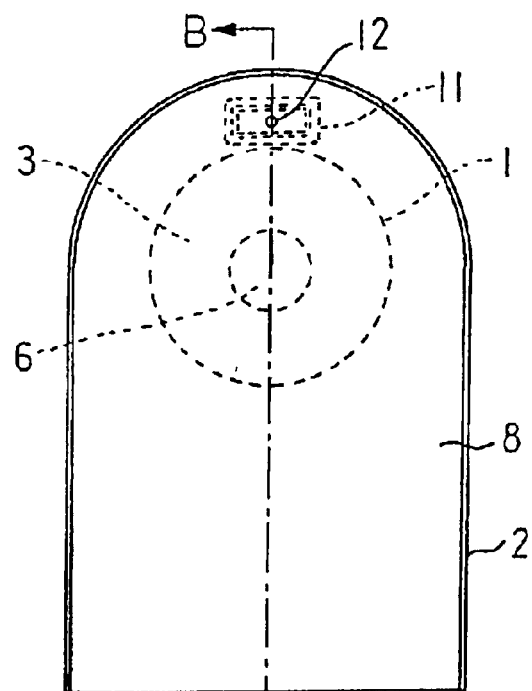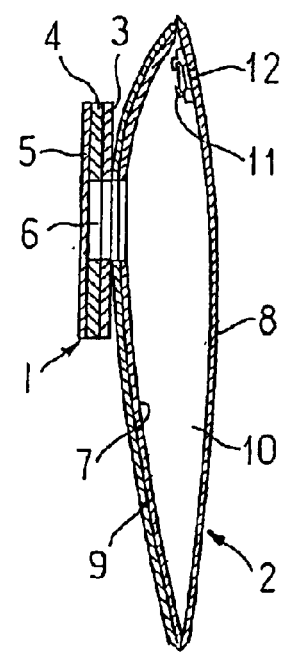
Fig. 1A
Fig. 1B
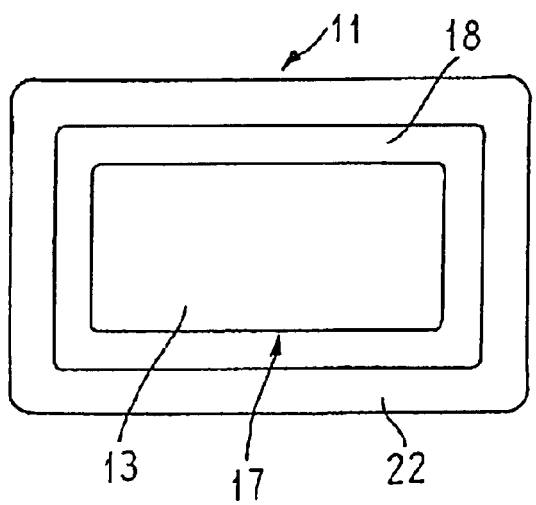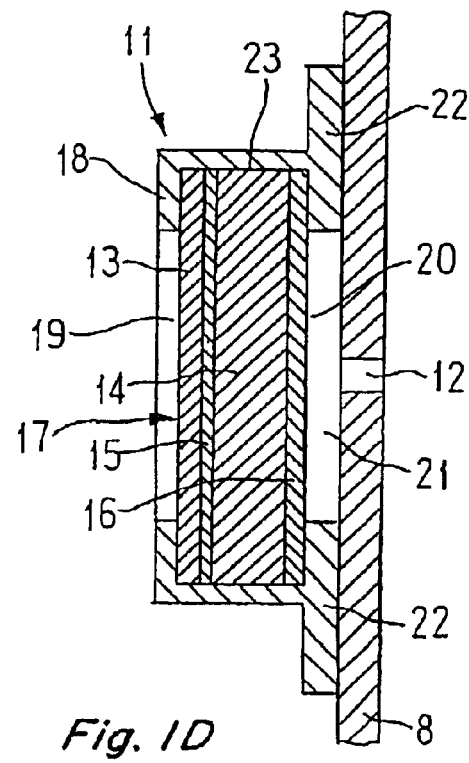
Fig. 1C
Fig. 1D

DEODORIZING FILTER AND COLLECTOR PROVIDED WITH THE DEODORIZING FILTER

Applicant hereby claims foreign priority benefits under 35 U.S.C. §119 of corresponding Japanese patent application No. 2001-198759, filed Jun. 29, 2001.

The present invention relates to a deodorizing filter adapted to be mounted to an ostomy bag or a container containing various contents that emit foul odors, irritating odors or sharp odors in order to let out the gases existing in the ostomy bag or container or the gases produced by the contents in the ostomy bag or container from within the ostomy bag or container, removing the odors, and the invention also relates to a collector provided with this deodorizing filter.

BACKGROUND OF THE INVENTION

A person who suffers the incontinence of feces and/or urine, a person who has undergone a surgical operation due to his digestive system disease, whereby his intestinal tract or urinary tract has been led out as far as the body surface and a stoma has been formed in the body surface, or a person who has a stoma or a fistula formed in the body surface due to a different disease, has the thus formed aperture equipped with a body wastes collector that can temporarily store the body wastes, in order to dispose of the body wastes such as feces, urine, body fluids, etc. discharged from the aperture formed in his body surface. This body waste collector generally comprises a faceplate and an ostomy bag. The faceplate is fixedly adhered to the portion around the aperture in the body surface by an adhesive layer of the faceplate and has the function of guiding the body wastes into the ostomy bag without allowing the leakage of the body wastes. In the body wastes, gases with odors are contained in some cases; and, as the body wastes are discharged, the gases also more and more increases in the ostomy bag, so that there is the danger that the ostomy bag may finally be ruptured unless the gases are suitably vented. Once the ostomy bag is ruptured, the body wastes leak out in a large quantity. In order to avoid the occurrence of such a state, it is practiced that a deodorizing filter is provided in a portion of the ostomy bag, so that the gases discharged into the ostomy bag are dissipated out of the ostomy bag, removing the odors by passing the gases through this deodorizing filter into the ostomy bag.

As the deodorizing filters that have so far been used in the body wastes collectors, there are known various types. As one feature of such filters, technical measures are taken to enhance the deodorizing effect by lengthening the flow path of the odorous gases that pass through the deodorizing element extending from the inside of the ostomy bag to the outside thereof. As the concrete structures according to such measures, the following ones are pointed out: The structure made in such a manner that a deodorant is accommodated at both sides of a spacer sheet disposed in a flat and hollow vessel, so that the gases are let to flow in through the deodorant portion at one side and then flow through passage holes provided in the spacer sheet into the deodorant portion at the other side, whereby the route through which the odors pass in contact with the deodorant is lengthened (See Japanese Patent Laid-Open No. (Hei) 8-103459); the structure made such that the gas passage extending between the gas inlet and the gas outlet of a case in which a deodorizing filter is incorporated is formed in a non-linear shape such as, e.g., a spiral shape, whereby the size of the case is miniaturized, and at the same time, the gas passage is lengthened (See Japanese Patent Application Laid-Open No. (Hei) 8-150165); the structure made such that a gas-discharging passage is formed along the outer periphery of the ostomy bag of a body wastes collector, and, at one end of this gas-discharging passage, an inlet communicating with the interior of the ostomy bag is formed, while, at the other end of the gas-discharging passage, an outlet communicating with the outside of the ostomy bag is formed, and the interior of the gas-discharging passage is filled up with a deodorant, whereby the route through which the gases flow in contact with the deodorant is lengthened, and at the same time, the thickness is decreased (See Japanese Patent Application Laid-Open No. (Hei) 9-253114); and the structure made such that a deodorizing filter is disposed horizontally in the upper portion of the ostomy bag of a body wastes collector, and the gas outlet thereof ends open in a space demarcated from the main space through which the body wastes in the ostomy bag are discharged, whereby the route through which the gas-discharging passage is lengthened, and at the same time, the outlet of the deodorizing filter is protected from the body wastes (See U.S. Pat. No. 6,328, 719). The measure of lengthening the flow passage of the odorous gases that pass through the deodorizing element of the deodorizing filter as stated above results in an enhancement of the deodorizing effect, but on the other hand, has the problematic point that the deodorant itself functions as a resistance to aggravate the gas permeability, and thus, the gas dissipation that is the intrinsic purpose becomes difficult.

Waste matters such as kitchen garbage, filth, etc. are collected by putting them into a garbage bag, in which case, in order to reduce the size of the garbage bag as much as possible, the work of squashing the bag from outside to draw out the air from inside the bag is carried out before sealing up the bag that has the waste matters put therein, but, when the bag is sealed up, the outside air flows into the bag again; and thus, the work of sealing up the bag must be repeated many times in some cases. In addition, when the air in the interior of the bag is vented, the offensive odor of the garbage is also given out, which gives an unpleasant feeling to not only the garbage collecting workers but also the other people around.

In case of preserving foods, more particularly, in case of preserving strong-scented foods, such foods are preserved by putting them in bags, vessels or the like so that the scent is not picked up by other foods, etc., in which case it is desirable to reduce their bulks by evacuating the gases in the interiors thereof as much as possible, in view of the efficient utilization of the food-reserving volumes. On the other hand, however, it is not so desirable to perfectly seal up foods such as fresh vegetables that respire. Further, of foodstuffs that are fermentation-processed, there are some that produce a carbonic acid gas, etc. during the process thereof; and therefore, there is the fear that the bags or the like that contain such foodstuffs may be ruptured if they are perfectly sealed up. Therefore, in case of such foodstuffs, it is desirable to perform gas venting in such a manner as to give a smelling influence to the surrounding area as little as possible and to keep the ventilation of air to the outside to a suitable degree.

Living things such as small animals, fishes, etc. discharge odorous feces and urine and emit peculiar smells of their own. In case a man moves carrying such living things or leaves them in a room temporarily, it is desirable to put them into vessels so as to allow the smells of the living things to be spread to the surrounding area as little as possible, but, they cannot be put into air-tight vessel since they are living things; and therefore, even in case they are put into vessels, it is necessary to maintain the circulation of air inside the vessel to the outside to a suitable degree so as not to disturb their respiration.

In case of keeping a chemical or a chemical substance that produces a gas with an offensive smell, it is necessary to ensure that the condition for keeping it in custody is appropriate and, further, to select a vessel that has a high hermetical sealability and is tough. Further, in case of reacting chemical substances with each other, a gas that emits an offensive smell or a foul smell is sometimes produced, so that it is necessary to manipulate a draft or to prepare a well-ventilated environment; and thus, the costs for keeping such chemical substances in custody or constructing the manufacturing facilities become higher.

OBJECTS OF THE INVENTION

It is an object of the present invention to provide a deodorizing filter that exhibits a good gas permeability in various uses, allows an easy discharge of the gases produced in a bag or a vessel and has a sufficient deodorizing ability. Another object of the invention is to provide a collector equipped with this deodorizing filter.

SUMMARY OF THE INVENTION

In order to achieve the above-mentioned object, the deodorizing filter according to the present invention is formed such that, in a housing, a deodorizing element is incorporated, and, at one side of the deodorizing element, a gas inlet is provided, while, at the other side, a gas outlet is provided, and a space exists at the side facing an ostomy bag to which the deodorizing element is to be mounted.

The housing for the deodorizing filter should desirably be formed in such a manner that a flange-shaped portion is provided at the side thereof to be fitted to the ostomy bag or that a surface thereof to face the inner side of the ostomy bag is formed into a rugged shape.

The deodorizing element of the deodorizing filter is closed in the outer periphery of the side surface thereof.

At the gas inlet side of the deodorizing element in the deodorizing filter, a gas-permeable water-proof film can be provided.

Further, the collector according to the invention is constituted such that, in the ostomy bag to accommodate therein the object to be deodorized, there is provided a gas outlet that connects the internal space of the ostomy bag to the outside, and the deodorizing filter is mounted so as to cover the gas outlet and so that a space formed in the deodorizing filter may face the ostomy bag. The deodorizing filter can be mounted to the inner side or the outer side of the ostomy bag.

BRIEF DESCRIPTION OF THE DRAWINGS

FIG. 1A is an overall front view of an embodiment of the deodorizing filter of the present invention applied to a body wastes collector;

FIG. 1B is a sectional view taken along the line B—B in FIG. 1A;

FIG. 1C is an enlarged front view of the filter of FIG. 1A;

FIG. 1D is an enlarged sectional view of an embodiment of the deodorizing filter according to the invention, wherein the magnification of FIG. 1D is larger than that of FIG. 1C;

DETAILED DESCRIPTION OF THE PREFERRED EMBODIMENTS

Figure 2:
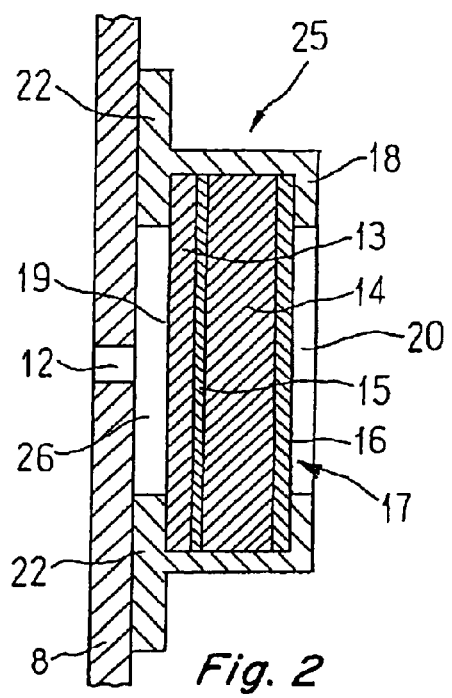
FIG. 2 is a sectional view of a different embodiment of the deodorizing filter according to the invention.

Shown in FIG. 1A is the application to a body wastes collector of the deodorizing filter according to the invention, wherein the reference numeral 1 denotes a faceplate for holding the body wastes collector onto the surface of a human body, and numeral 2 denotes an ostomy bag that is fitted to the faceplate to collect the body wastes. Also referring to FIG. 1B, the faceplate 1 comprises a flange layer 3, an adhesive layer 4 and a release film 5; these members being formed integrally, with the adhesive layer 4 disposed at the human body side, that is, the skin-contacting side, and, in the center portion of the faceplate 1, an opening 6 is provided. The ostomy bag 2 is fixed onto the flange layer 3 at the non-skin-contacting side of the faceplate 1 and is constituted so as to receive the body wastes discharged through the opening 6 in the faceplate 1 from the aperture in the human body to which the faceplate 1 is coupled by means of the adhesive layer 4. The ostomy bag 2 comprises an inner side (the human body side) film 7 and an outer side (the side opposite with respect to the human body) film 8, and, at that side of the inner side film 7 which is close to the skin, a non-woven fabric 9 is disposed in order to prevent the occurrence of a sticky feeling and a sweaty state due to the contact between the skin and the inner side film 7; and the inner side film 7, the outer side film 8 and the non-woven fabric 9 are sealed together in the peripheral portion thereof by means of, e.g., heat sealing to form an inner space 10. Numeral 11 denotes a deodorizing filter, which is mounted onto the upper portion of the inner surface of the outer side film 8, and, in the outer side film 8, there is provided a gas outlet 12 through which the deodorizing filter 11 communicates with the outside. The shape of this gas outlet 12 is not particularly limited; the gas outlet 12 can be made in the form of a U-shaped, V-shaped, or straight slit, etc., or a circular, oval or otherwise shaped hole. One or more such slits or holes can be provided. The gas outlet 12 and the deodorizing filter 11 that covers the gas outlet 12 should desirably be set in a portion higher than the opening 6, in the state in which the body wastes collector is normally used. This is because, if the filter is disposed at the position facing the opening 6 or at a position lower than the opening 6, then the filter is apt to be soiled by the body wastes.

Referring also to FIGS. 1C and 1D, the deodorizing filter 11 is constituted such that a deodorizing element 17 is incorporated in a housing 18; the deodorizing element 17 is constituted such that a gas-permeable, water-proof film 13 and a deodorant 14 are stuck to each other by means of a reticulate hot-melt adhesive 15, and, to that surface of the deodorant 14 which lies at the opposite side with respect to the gas-permeable, water-proof film 13, a porous sheet 16 is stuck. The housing 18 is formed in the shape of a flat rectangular parallelepiped in this embodiment and constituted such that a gas inlet 19 is provided at that side of the housing 18 which lies close to the gas-permeable, waterproof film 13, while a gas outlet 20 is provided at that side of the housing 18 which lies close to the porous sheet 16, and, on that surface of the housing 18 which lies at the side of the porous sheet 16 facing the outer side film 8 of the ostomy bag 2, a space 21 exists between the above-mentioned surface and the outer side film 8, so that the gases that have passed through the porous sheet 16 are not directed against the outer side film 8; but, in the housing 18, the gases can flow out from the whole surface of the outlet 20 in the deodorizing element 17. As one method for assuring such constitution, the housing 18 may be formed in such a manner as to have a flange portion 22 with a suitable thickness at that side of the housing 18 which faces the outer side film 8. The filter is desirably formed in such a manner that, in the space 21 thus formed, the distance from the deodorizing element 17 to the outer side film 8 is about 0.2 mm or greater; if the filter is of the structure in which the distance from the deodorizing element 17 to the outer side film 8 is the above-mentioned value or greater, a smooth gas venting can be made. Further, the housing 18 is desirably formed so as to cover, at the gas inlet side, the outer periphery 23 of the side surface of the deodorizing element 17 to thereby prevent the gases from flowing in from the side surface; if otherwise, the route through which the gases are contacted with the deodorizing element 17 would be shortened. The flange-shaped portion 22 of the housing 18 of the deodorizing filter 11 is fixed by, e.g., heat sealing to the inner wall of the outer side film 8. Further, as for the housing structure, a housing constituted such that the surface of the housing which faces the inner side of the ostomy bag is formed in a rugged state can alternatively be used. In case the filter is flat, the wall portion at that position of the ostomy bag which faces the filter closely attaches to the gas inlet of the filter to thereby block the flow-in of the gas in some cases, but, by providing this rugged surface, the blockade of the gas inlet can be prevented.

As for the materials constituting the faceplate 1 and the ostomy bag 2, there can be used materials similar to the materials conventionally used. For the flange layer 3 of the faceplate, materials such as polyethylene, ethylene-vinyl acetate copolymer, ethylene-ethyl acrylate copolymer, ethylene-methyl acrylate copolymer, polypropylene, polyvinyl chloride, polyester, polyamide, etc. can be used either singly or in combination. For the adhesive layer 4, there can be used a skin protecting agent consisting of a hydrophilic polymer and a hydrophobic polymer. For both films 7, 8 of the ostomy bag 2, there can be used single-component films consisting of polyvinylidene chloride, polyethylene, polyvinyl chloride, and chlorinated polyethylene, or composite films prepared by blending or copolymerizing these components with vinyl acetate, polyacrylic acid, etc. For the non-woven fabric 9, there can be used, for example, a polypropylene-polyethylene conjugate non-woven fabric.

For the gas-permeable, water-proof film 13 of the deodorizing filter 11, materials that are gas-permeable, water-proof and, further, free from lipid penetration are most suitable; and there can be used Versapore 1200 R (commodity name; manufactured by Nihon Pall, Ltd.) consisting of polyamide/modified acrylic polymer non-woven fabric. For the deodorant 14, granular activated charcoal or fibrous activated charcoal are usable, and FMS-186S (commodity name; manufactured by Unitika, Ltd.), which is a fibrous activated charcoal, is preferred. For the reticulate hot melt adhesive 15, materials such as polyamide, ethylene-vinyl acetate copolymer, polyethylene, etc. can be used singly or in composite form. For the porous sheet 16 that is to be applied to that surface of the deodorant 14 which is opposite to the gas-permeable, water-proof film 13, there can be used CE 15 or SN-9 (commodity name; manufactured by Smith & Nephew Inc.) which is a porous laminated sheet consisting of a thermoplastic resin. The housing 18 incorporates the deodorizing element therein and should desirably be comprised of a material having a hardness sufficient to ensure that, even if the housing 18 is subjected to an external force—which is applied when the user wears the body wastes collector—such as, e.g., the friction caused by the user's body and clothes, the pushing force applied at the time of gas venting, and the user's body weight when he or she lies down, the shape of the housing and the space portion formed in the interior thereof are not easily deformed; as such a material, a material that has a hardness of 30 or higher as measured in accordance with the "durometer hardness of plastics (Type A)" of JIS K 7215 is preferable. As such a material, a thermoplastic plastics material such as polyethylene, ethylene-vinyl acetate copolymer, polypropylene or the like can be used in view of the ease with which the material can be processed, the ease with which the material can be applied to the film of the ostomy bag by heat sealing.

When the user puts on the body wastes collector shown in FIG. 1, the release film 5 of the faceplate 1 is removed, and the body wastes collector is attached to the surface of the user's body through the adhesive layer 4 after the opening 6 of the faceplate 1 is aligned with the aperture formed in the user's body. The body wastes discharged through the aperture in the human body pass through the opening 6 in the faceplate 1 into the internal space 10 of the ostomy bag 2. The gases and odors produced from the body wastes pass through the gas-permeable, water-proof film 13, the reticulate hot melt adhesive 15, the deodorant, 14, and the porous sheet 16 and then through the space 21 formed in the housing 18 in a state surrounded by the porous sheet 16, the outer side film 8, and the side wall of the housing 18 and are then dissipated to the outside via the gas outlet 12 of the outer side film 8. In this case, the body wastes are blocked by the gas-permeable, water-proof film 13, while the odors are adsorbed or changed by the deodorant 14 into at least substantially odorless substances, thus passing through the interior of the deodorizing filter.

FIG. 2 shows a different embodiment of the deodorizing filter, wherein portions identical with those shown in FIG. 1 are referenced by the same reference numerals. A deodorizing filter 25 is mounted on the outer surface of the outer side film 8 and communicates with the internal space 10 (FIG. 1B) of the ostomy bag through the gas outlet 12 in the outer side film 8. The deodorizing filter 25 is constituted such that, in the housing 18, there are incorporated the gas-permeable, water-proof film 13, the reticulate hot melt adhesive 15, the deodorant 14 and the porous sheet 16 as in the case of the embodiment shown in FIG. 1, but they are disposed in the opposite order; that is, at the side facing the outer side film 8, i.e., at the flange-shaped portion 22 side of the housing 18, the gas-permeable, water-proof film 13 is disposed, and, between the gas-permeable, water-proof film 13 and the outer wall of the outer side film 8, that is, at the gas inlet 19 side of the deodorizing filter, a space 26 is provided. The gases discharged through the gas outlet 12 from within the ostomy bag are passed through the deodorizing filter 25 and then discharged to the outside, in which case the passage of the body wastes is blocked by the gas-permeable, water-proof film 13, while the odorous gases pass through the deodorant 14, whereby the odors can be absorbed or changed into at least substantially odorless substances. In case of this type of body wastes collector, the deodorizing filter 25 can be easily replaced from outside.

Figure 3A:
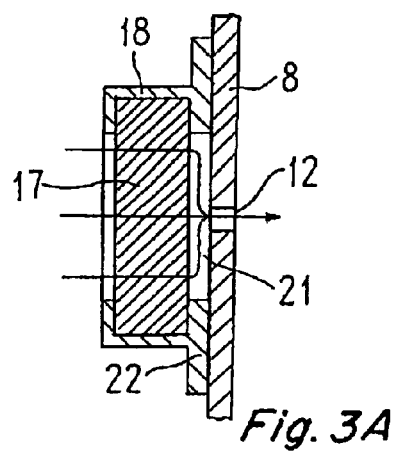
FIG. 3A shows a diagram explaining the function of the deodorizing filter according to the invention.
Figure 3C:
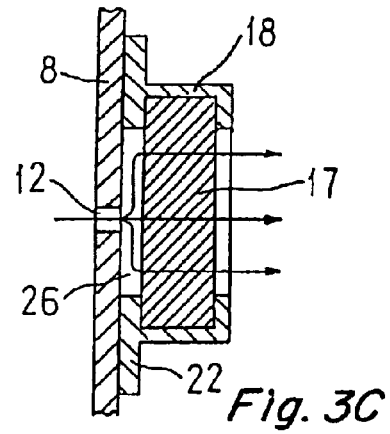
FIG. 3C shows another diagram explaining the function of the deodorizing filter according to the invention.
Figure 3B:
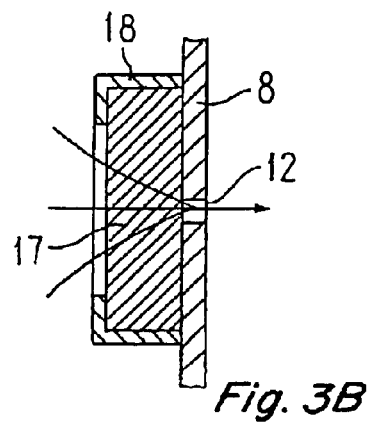
FIG. 3B shows another diagram explaining the function of the deodorizing filter according to the invention.
Figure 3D:
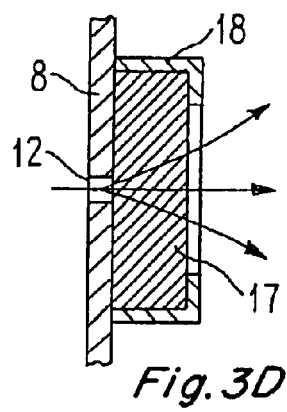
FIG. 3D shows another diagram explaining the function of the deodorizing filter according to the invention.

FIGS. 3A, 3B, 3C and 3D show diagrams explaining the flow of the gases in the deodorizing filter according to the present invention. FIG. 3A shows a deodorizing filter constituted such that the deodorizing filter shown in FIG. 1 is mounted on the inner side of the film forming the ostomy bag, FIG. 3B shows a deodorizing filter constituted such that, in the deodorizing filter shown in FIG. 3A, the flange-shaped portion of the housing is not provided, so that the deodorizing filter is mounted in such a manner that the gas outlet side of the deodorizing element is directly and closely attached to the inner wall of the ostomy bag, FIG. 3C shows a deodorizing filter constituted such that the deodorizing filter shown in FIG. 2 is mounted on the outer side of the film forming the ostomy bag, and FIG. 3D shows a deodorizing filter constituted such that, in the deodorizing filter shown in FIG. 3C, the flange-shaped portion of the housing is not provided, and the deodorizing filter is mounted in such a manner that the gas inlet side of the deodorizing element is directly and closely attached to the outer wall of the film constituting the ostomy bag. In the respective diagrams mentioned above, arrows indicate the flow of the gases.

In the case of FIG. 3B and FIG. 3D, the gas outlet side or the gas inlet side of the deodorizing element is closely attached to the ostomy bag, so that the gases are subjected to the resistance of the film surface of the ostomy bag at the gas outlet or the gas inlet of the deodorizing element 17 and thus rate-determined here, as a result of which the permeability assumes a high value. In contrast, in the case of the deodorizing filter of the present invention shown in FIG. 3A and FIG. 3C, the space 21 or 26 exists at that side, which faces the ostomy bag, of the housing 18 with the deodorizing element 17 incorporated therein, so that, in case of FIG. 3A, the gases flowing in from the inlet side of the deodorizing element 17 pass through the whole region of the deodorizing element and flow out into the space 21 in the housing 18 and is then discharged from the gas outlet 12 of the ostomy bag, while, in case of FIG. 3C, the gases discharged from the gas outlet 12 of the ostomy bag flow into the space 26 of the housing 18, in which case, even if the gas outlet 12 of the ostomy bag is of a small area, the gas flow passage expands in said space 26, and thus, the gases pass through the whole region of the deodorizing element 17 and then discharged from the gas outlet of the deodorizing filter. Thus, the gases are not subjected to the resistance of the film surface of the ostomy bag, so that the gases are not rate-determined by the film surface; and the permeability is suppressed to a low value. The permeability was measured in case the distance from the surface of the film 8 constituting the ostomy bag to the deodorizing element 17 was set to 1 mm in the cases of FIG. 3A and FIG. 3C, while the same distance was set to 0 mm in the cases of FIG. 3B and FIG. 3D, as a result of which, in case of FIG. 3A, the value of permeability obtained was 23.9 sec/300 ml•Air, whereas, in case of FIG. 3B, the value of permeability obtained was 45.2 sec/300 ml•Air; and, in case of FIG. 3C, the value of permeability obtained was 24.5 sec/300 ml•Air, whereas, in case of FIG. 3D, the value of permeability obtained was 45.1 sec/300 ml•Air. Thus, according to the present invention, the value of permeability is reduced to about half; an appropriate permeability is achieved. The permeability as used in the present specification indicates the values obtained by measurement according to 6.272.B Method under the "JIS L 1096, 6.27 Permeability" and represents the time required when 300 ml of air is ejected through a test material under a load of 1.39 N.

Further, as for the deodorizing ability, in accordance with British Industrial Standard 7127 (Ostomy collection bags Part 101. Specification for one-piece and two-piece ostomy collection systems), 30 ppm of hydrogen sulfide was passed through the deodorizing element, and the time spent until the concentration of hydrogen sulfide after the passage thereof through the deodorizing element reached 1 ppm was measured to confirm the performance in respect of the deodorizing ability. In accordance with this test method, the preferred deodorizing ability is defined as 10 minutes or longer; and, as the filter used in the present invention, a filter which satisfies this value requirement can desirably be used. In case of this embodiment, the fibrous activated charcoal, FMS 186S (manufactured by Unitika Ltd.), which had a surface with a size of 20 mm×10 mm and had a thickness of 2 mm (a volume of 400 mm$^3$) was used; and the deodorizing ability lasted for about 200 minutes.

So far, there exists a deodorizing filter structure constituted such that a depression is formed in a film constituting an ostomy bag, a gas outlet is provided in the depression, and a deodorizing filter is mounted in a state facing this depression. According to this deodorizing filter structure, a space can be provided between the deodorizing filter and the ostomy bag, so that the permeability is improved. However, since the film constituting the ostomy bag is normally formed of a thin thermoplastic resin film, it is possible to form a space portion by forming a depression in the film by the use of, e.g., an embossing die, but the depression is easily deformed, and thus, the advantageous function of the space portion cannot be continuously maintained. Further, it is not easy to form a clearly defined depression in a thin film, so that, a special processing step is required for forming such a clearly defined depression. In this respect, according to the present invention, the deodorizing element is incorporated in a housing that has a suitable hardness, and a space is formed in this housing, so that the function of the space portion can be continuously maintained, and in addition, any additional step for processing the ostomy bag itself is not needed; and thus, the deodorizing filter can be mass-produced as a finished article separately from the ostomy bag; and the deodorizing filter as a finished article can be easily mounted to the wall of the ostomy bag without performing any special processing work. This point is very advantageous in view of the manufacture, and therefore, the deodorizing filter also possesses general-purpose properties as a part. Further, due to the recent improvement in the performance of deodorants, a sufficient deodorizing effect can be achieved without particularly lengthening the gases' route of contact with the deodorant.

In the above-described embodiments, a rectangular shape is used as the shape of the housing of the deodorizing filter, but it is not limited to such a rectangular shape, but a circular or any other shape can also be employed.

Further, the foregoing embodiments have been described as those of the so-called one-piece type in which the faceplate and the ostomy bag are direct-coupled to each other, but it is apparent that the present invention can also be applied to the so-called two-piece type in which the faceplate and the ostomy bag can be separated from each other. Further, the foregoing embodiments have been described as those of the type in which the gas outlet and the deodorizing filter covering it are disposed on the outer side film (the side opposite to the user's body) of the ostomy bag, but it is alternatively possible to apply the present invention in such a manner that the gas outlet and the deodorizing filter covering it are mounted on the inner side film (the side close to the user's body) of the ostomy bag. In this case, it is also a matter of course that the gas outlet and the filter should desirably be provided above the opening.

In case the deodorizing filter according to the present invention is applied to a body waste collector, the gas permeability of the deodorizing filter is markedly enhanced, so that, even if the interior of the ostomy bag is filled up with gases, the gases can be smoothly discharged through the deodorizing filter without applying a strong force; and thus, a person wearing this body wastes collector can lead his daily life without fearing that the body wastes may leak out, that the ostomy bag may be ruptured when a large amount of the gases is stored in the ostomy bag by an unexpected excretion, or that the faceplate may come off due to a conspicuous rise in the pressure in the ostomy bag. Further, in view of the manufacture of body wastes collectors, the deodorizing filter can be mounted onto a body wastes collector by a simple manufacturing step and thus is also advantageous in respect of the cost. Moreover, the deodorizing filter can be accommodated in a small size.

Figure 4A:
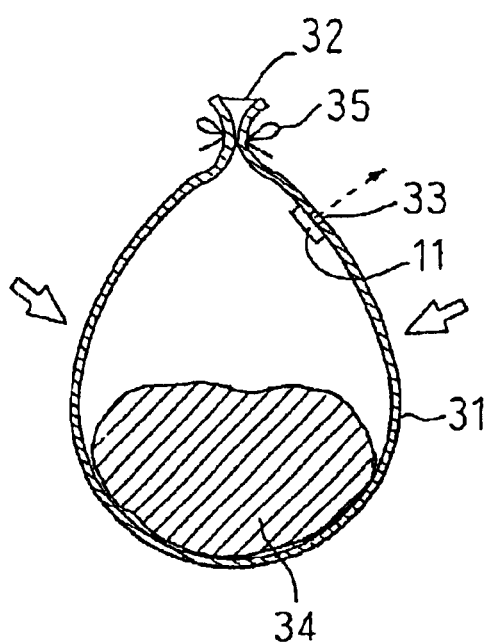
FIG. 4A is a sectional view of an embodiment of the invention shown applied to a garbage bag.
Figure 4B:
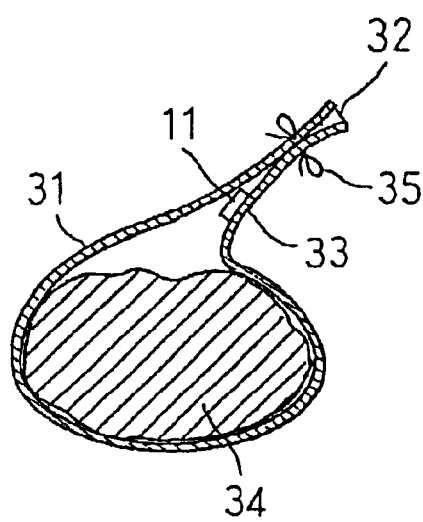
FIG. 4B is another sectional view of the embodiment of the invention of FIG. 4A and the garbage bag, the bag being shown in a compacted condition.

FIGS. 4A and 4B show the case in which the deodorizing filter according to the present invention is mounted on the inner side of a garbage bag. The reference numeral 31 denotes a garbage bag consisting of, e.g., a polyethylene film. The garbage bag 31 has an opening 32, and, in one portion of the bag, there is provided a gas outlet 33 which connects the internal space of the bag and the outside to each other; and the deodorizing filter 11 shown in FIG. 1C and FIG. 1D is mounted on the inner surface of the bag 31 so as to cover the gas outlet 33. FIG. 4A shows the state in which garbage 34 is collected in the garbage bag 31, and the opening 32 is sealed up as shown by numeral 35. In this state, air remains in the interior of the bag 31, and thus, the bulk of the bag 31 is very large as compared with the amount of garbage 34. Thus, after the opening 32 is sealed up as shown by numeral 35, the outer side of the bag 31 is pushed up as shown by thick-lined arrows, whereby the air inside is pushed out through the air passage of the deodorizing filter 11 as shown by a broken-line arrow, as a result of which the bulk of the bag 31 is reduced to the net amount of the garbage 34 as shown in FIG. 4B.

Shown in FIGS. 4A and 4B is the case in which the deodorizing filter is mounted on the inner side of the garbage bag, but the deodorizing filter may alternatively be mounted on the outer side of the garbage bag. By mounting the deodorizing filter on the inner side or the outer side of the garbage bag, the air inside the garbage bag can be let out after the garbage bag is sealed up, so that any extra air does not flow into the bag from outside, gas venting can be efficiently carried out without being affected by the foul odors of the garbage. Further, even if the gas volume of gases in the bag is increased again by the generation of gases due to, e.g., the decomposition of the contents in the bag, the gases in the bag can be vented without opening the sealed bag in each such occasion. Further, by providing a gas-permeable, water-proof film at the gas inlet side of the deodorizing filter, it becomes possible to avoid the influence by the water from the garbage, etc.

By using the deodorizing filter of the invention in a bag for preserving foodstuffs, the extra gases can be vented without allowing the smell of the foodstuffs to leak outside the bag, and further, even in case gases are produced in the bag due to the fermentation of the foodstuffs, etc., the gases in the bag can be vented without opening the sealed bag and that without being affected by the odors. Moreover, by providing the gas-permeable, water-proof film at the gas inlet side of the deodorizing filter, it becomes possible to avoid the influence by the water from the foodstuffs.

In case the deodorizing filter according to the invention is applied to a bag for keeping or carrying a living thing, the living thing in the bag can respire since the inside and the outside of the bag communicate with each other through the deodorizing filter; and the discharge of the air inside the bag is performed through the deodorizing filter, so that the smell of the living thing does not leak out. In particular, in case of carrying a small animal, if the air inside is temporarily vented to reduce the bulk of the bag, it is convenient for carrying the bag. Further, in case the size of the bag is a standard size, the extra gas can be vented in conformity with the size of the living thing to be put into the bag so as to keep the bag in a suitable size. Moreover, by providing the gas-permeable, water-proof film at the gas inlet side of the deodorizing filter, the influence by the water, etc. emitted from the living thing can be eliminated.

By using the deodorizing filter according to the invention in a vessel for containing chemicals, chemical substances or the like, it becomes possible to ensure that the gases generated can be discharged through the deodorizing filter mounted in a general-purpose vessel used and without taking any special measure for the air-tight sealing of the vessel; and thus, the expenses for handling the chemicals, chemical substances, etc. can be reduced, and in its turn, manufactured goods can be provided at low prices. Moreover, it is possible to prevent the cover of a vessel from springing off and to prevent the vessel from being partially broken. In case chemical substances are mixed and reacted with each other in a vessel or bag equipped with the deodorizing filter according to the invention, the gas produced is suitably discharged through the deodorizing filter, so that the rupture or the like of the vessel or the bag is not caused, nor is any adverse effect exerted on the surrounding environment by the foul odor, etc. of the gas produced.

As has been stated above, particularly in case the deodorizing filter according to the invention is applied to a bag or vessel formed of a material such as, particularly, a plastics film that is soft and flabby, the passage of the gas is always secured even if the plastics film is bent, since a space is formed, by the housing of the deodorizing filter, between the deodorizing filter and the plastics film; and thus, the gas can flow smoothly.

Thus, there has been shown and described several embodiments of a deodorizing filter and collector provided with the deodorizing filter, which fulfills all of the objects and advantages sought therefor. Many changes, modifications, variations, and other uses and applications of the present construction will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. A deodorizing filter comprising a deodorizing element for deodorizing gases which pass therethrough, the deodorizing element having a first side, another side, and an outer periphery of the sides, and said deodorizing element being contained in a housing having a flanged-shaped portion, and, at the first side of said deodorizing element, a gas inlet is provided, while, at another side of the deodorizing element a gas outlet is provided, said housing being mounted, at its flanged-shaped portion, to an ostomy bag containing gases to be deodorized such that the gas inlet is connected to an inner space of the bag containing the gases for receiving the gases therefrom, and a space exists between the first side of the deodorizing element and the gas inlet and the outer periphery of the sides of said element being closed by the housing.

2. The deodorizing filter according to claim 1, wherein the housing has a ruggedness on that surface thereof which faces the inner side of the ostomy bag.

3. The deodorizing filter according to claim 1, wherein a gas-permeable, water-proof film is provided in covering relation to the first side of the deodorizing element.

4. The deodorizing filter according to claim 1, wherein the deodorizing element has a deodorizing ability for deodorizing gases which pass therethrough which lasts for about 10 minutes or more.

5. A body wastes collector comprising a deodorizing filter that covers a gas outlet provided in a side of an ostomy bag so as to connect an internal space of the ostomy bag for collecting body wastes to an outside of said ostomy bag, said deodorizing filter being formed so as to incorporate a deodorizing element in a housing, which housing has a flanged-shaped portion mounted to the ostomy bag, and having a gas inlet at one side of the deodorizing element, a gas outlet at another side of the deodorizing element, and said deodorizing element having an outer periphery of its sides which is closed, and a space existing between the one side of said deodorizing element and the gas inlet, and the gas inlet being connected to the gas outlet of said ostomy bag.

6. The collector according to claim 5, wherein the deodorizing filter is mounted on an inner surface of the side of the ostomy bag.

7. The collector according to claim 5, wherein said deodorizing filter is mounted on an outer surface of the side of said ostomy bag.

* * * * *